United States Patent
Pijl

(10) Patent No.: US 9,560,619 B2
(45) Date of Patent: Jan. 31, 2017

(54) METHOD OF ESTIMATING THE POSITION OF A DEVICE AND AN APPARATUS IMPLEMENTING THE SAME

(71) Applicant: KONINKLIJKE PHILIPS N.V., Eindhoven (NL)

(72) Inventor: Marten Jeroen Pijl, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 74 days.

(21) Appl. No.: 14/408,620

(22) PCT Filed: Jun. 17, 2013

(86) PCT No.: PCT/IB2013/054933
§ 371 (c)(1),
(2) Date: Dec. 17, 2014

(87) PCT Pub. No.: WO2014/001947
PCT Pub. Date: Jan. 3, 2014

(65) Prior Publication Data
US 2015/0173037 A1 Jun. 18, 2015

Related U.S. Application Data

(60) Provisional application No. 61/665,359, filed on Jun. 28, 2012.

(51) Int. Cl.
*G01S 19/42* (2010.01)
*H04W 64/00* (2009.01)
(Continued)

(52) U.S. Cl.
CPC ............ *H04W 64/00* (2013.01); *A61B 5/1117* (2013.01); *G01C 21/005* (2013.01); *G01S 19/49* (2013.01);
(Continued)

(58) Field of Classification Search
CPC ........ H04W 64/00; H04W 4/02; H04W 4/023; H04W 4/028; H04W 64/003; H04W 4/025; G01S 19/40; G01S 19/42; G01S 19/25; G01S 19/14; G01S 19/35; G01S 5/021; G01S 19/07; G01S 19/51; G01S 5/0036; G01S 5/0257; G01S 5/0263
(Continued)

(56) References Cited

U.S. PATENT DOCUMENTS 6,486,831 B1   11/2002   Martorana et al.
6,496,695 B1 *  12/2002  Kouji ............... A61B 5/1112
                                                       340/853.2

(Continued)

FOREIGN PATENT DOCUMENTS

EP   2426511 A1   3/2012
JP   20060166421 A   6/2006

OTHER PUBLICATIONS

Reddy et al, "Using Mobile Phones to Determine Transportation Modes", ACM Transactions on Sensor Networks, vol. 6, No. 2, Article 13, 2010, pp. 1-27.
(Continued)

*Primary Examiner* — Olumide T Ajibade Akonai

(57) ABSTRACT

There is provided a method of detecting erroneous measurements of the position of a device, the device comprising position measurement means, the method comprising determining the state of motion of a user of the device from a plurality of possible states; predicting the position of the device using a plurality of models and the determined state of motion of the user, each model corresponding to a respective one of the plurality of possible states; measuring the position of the device using the position measurement means; comparing the predicted position of the device to the measured position of the device; and determining whether
(Continued)

the measured position of the device is erroneous based on the result of the step of comparing.

19 Claims, 2 Drawing Sheets

(51) Int. Cl.
  *A61B 5/11*  (2006.01)
  *G01C 21/00*  (2006.01)
  *G01S 19/49*  (2010.01)
  *G01S 19/40*  (2010.01)
  *A61B 5/00*  (2006.01)

(52) U.S. Cl.
  CPC ...... *A61B 5/0022* (2013.01); *A61B 2562/0219* (2013.01); *G01S 19/40* (2013.01); *G01S 19/42* (2013.01)

(58) Field of Classification Search
  USPC .............. 455/456.1–456.6; 342/357.25
  See application file for complete search history.

(56) References Cited

U.S. PATENT DOCUMENTS

| | | | |
|---|---|---|---|
| 2001/0012324 A1* | 8/2001 | Normile | H04N 19/52 375/240.05 |
| 2003/0151501 A1 | 8/2003 | Teckchandani et al. | |
| 2006/0211430 A1* | 9/2006 | Persico | G01S 5/0263 455/456.1 |
| 2007/0049289 A1* | 3/2007 | Woo | G01S 5/0027 455/456.1 |
| 2007/0271032 A1* | 11/2007 | Cheng | G01S 5/0294 701/2 |
| 2008/0005036 A1* | 1/2008 | Morris | A47F 9/047 705/64 |
| 2009/0201149 A1 | 8/2009 | Kaji | |
| 2010/0179757 A1 | 7/2010 | Iketani et al. | |
| 2011/0084874 A1* | 4/2011 | Coatantiec | G01S 19/20 342/357.3 |
| 2011/0090115 A1* | 4/2011 | Gum | G01S 19/05 342/357.42 |
| 2011/0228810 A1* | 9/2011 | O'Hara | G01J 5/0003 374/121 |
| 2012/0136573 A1 | 5/2012 | Janardhanan et al. | |
| 2013/0045760 A1* | 2/2013 | Obermeyer | G08B 21/0277 455/456.6 |
| 2013/0154879 A1* | 6/2013 | Ramakrishnan | G01S 19/426 342/357.25 |
| 2014/0368386 A1* | 12/2014 | Mansour | G01S 5/0294 342/461 |

OTHER PUBLICATIONS

Foerster et al, "Detection of Posture and Motion by Accelerometry: A Validation Study in Ambulatory Monitoring", Computers in Human Behaviour, vol. 15, 1999, pp. 571-583.
Nick et al, "Classifying Means of Transportation Using Mobile Sensor Data", Neural Networks (IJCNN), Jul. 2010, pp. 1-6.
Li et al: "Deformation Detection in the GPS Real-Time Series by the Multiple Kalman Filters Model"; Journal of Surveying Engineering, Nov. 2010; pp. 157-164.
Malleswari et al: "The Role of Kalman Filter in the Modelling of GPS Errors; Journal of Theoretical and Applied Information Technology"; 2005, pp. 95-101.
Ashbrook et al: "Using GPS to learn Significant Locations and Predict Movement Across Multiple Users"; Personal and Ubiquitous Computing, Oct. 2003, Issue 5, pp. 275-286.

* cited by examiner

METHOD OF ESTIMATING THE POSITION OF A DEVICE AND AN APPARATUS IMPLEMENTING THE SAME

CROSS-REFERENCE TO PRIOR APPLICATIONS

This application is the U.S. National Phase application under 35 U.S.C. §371 of International Application Serial No. PCT/IB2013/054933, filed on Jun. 17, 2013, which claims the benefit of U.S. Application Ser. No. 61/665,359, filed on Jun. 28, 2012. These applications are hereby incorporated by reference herein.

TECHNICAL FIELD OF THE INVENTION

The invention relates to portable or mobile devices that include a receiver, such as a satellite positioning system receiver, the measurements from which are used to provide a measurement of the position of the device.

BACKGROUND TO THE INVENTION

Currently, satellite positioning systems, such as GPS, are one of the most accurate location data sources available to portable or mobile electronic devices. However, there are a number of drawbacks associated with satellite positioning systems. For example, it might not be possible to receive signals from the satellites when the device is indoors, under heavy foliage or in an 'urban canyon' (i.e. between a number of tall buildings), making it impossible to obtain a position measurement (sometimes referred to as a 'fix'). Satellite positioning systems can also be prone to errors in the position measurement which can be due to a number of different reasons, including 'multipathing' where the signals from a satellite can reflect off of buildings before reaching the satellite positioning system receiver. These errors can cause the reported position to be some distance from the actual position, sometimes even as far as several city blocks. These erroneous measurements are sometimes referred to as 'outliers'.

GPS-enabled devices can be used to track the location of a user carrying the device. Users of such devices can include elderly people, children, people with Alzheimer's disease or dementia (who are prone to wandering) or patients in a care home or hospital. In some of these cases, 'geofences' can be established that bound safe or acceptable areas in which the user is allowed to move freely (or conversely areas that the user should not enter). Any obtained position measurement is compared to the geofence, and if the user is found to be outside the geofence (i.e. in an area that they should not be in), an alarm can be triggered or an alert raised. The position measurements obtained by the device can be provided to a remote location, such as a call centre or emergency services personnel, to enable the device and thus the user to be found.

It will be appreciated that in geo fencing applications, outlier position measurements can indicate that the user is outside the acceptable area and can result in an alarm being triggered, when in fact the user is within the acceptable area. The alarm can be provided for the benefit of the user (i.e. the alarm can be audible to the user of the device to indicate that they have crossed the geofence), or the alarms can be used to initiate the dispatch of people or the emergency services to locate and help the user of the device. Likewise, outlier position measurements can indicate that the user is within the acceptable area when in fact the user has crossed the geofence, which means that an alarm might not be triggered. Therefore, it is desirable to minimise false alarms caused by outliers.

Even if an alarm is correctly triggered (i.e. the user has crossed the geofence), outlier measurements relayed to the emergency services or other person dispatched to find the user can send that person off in the wrong direction and delay the assistance being provided to the user.

Therefore, there is a need for an improved technique to identify outlier position measurements.

SUMMARY OF THE INVENTION

According to a first aspect of the invention, there is provided a method of detecting erroneous measurements of the position of a device, the device comprising position measurement means, the method comprising determining the state of motion of a user of the device from a plurality of possible states; predicting the position of the device using a plurality of models and the determined state of motion of the user, each model corresponding to a respective one of the plurality of possible states; measuring the position of the device using the position measurement means; comparing the predicted position of the device to the measured position of the device; and determining whether the measured position of the device is erroneous based on the result of the step of comparing. Thus, the invention improves the accuracy of the predicted positions by adapting the prediction algorithm to the current state of motion of the user, which makes erroneous measurements from the position measurement means easier to identify.

Preferably, the plurality of possible states comprises two or more of the user sitting down, lying down, standing still, walking, running and traveling in a vehicle.

Preferably, the step of determining the state of motion of the user comprises analysing signals from one or more sensors and/or one or more earlier measured positions of the device. In some embodiments, the signals from one or more sensors comprise signals from one or more of an accelerometer, magnetometer and gyroscope.

In some embodiments, the step of determining the state of motion of the user comprises analysing the signals from the one or more sensors to identify signals indicative of footsteps by the user and/or the orientation of the user.

In some embodiments, the step of predicting the position of the device comprises using each of the plurality of models to estimate the next position of the device; weighting the estimate of the next position of the device obtained from each of the models according to the determined state of motion of the user; and combining the weighted estimates to determine the predicted position of the device.

In alternative embodiments, the step of predicting the position of the device comprises selecting the one of the plurality of models corresponding to the determined state of motion of the user; and using the selected one of the plurality of models to determine the predicted position of the device.

In preferred embodiments, the plurality of models use dead-reckoning to estimate the position of the device. In further preferred embodiments, the plurality of models further use map data indicating roads and/or walkways to estimate the position of the device. This improves the accuracy of the predicted position of the device further by limiting the predicted position to positions that are consistent with the determined state of motion of the user (i.e. on the road if determined to be traveling in a vehicle and on a walkway if determined to be on foot—whether standing, walking or running).

Preferably, the method is implemented using a Kalman filter, and wherein the step of predicting the position of the device comprises using a plurality of models, the determined state of motion of the user and a current state of the Kalman filter.

Preferably, in a Kalman filter, the result of the step of comparing the predicted position of the device to the measured position of the device is used to update the current state of the Kalman filter.

Preferably, the step of determining whether the measured position of the device is erroneous based on the result of the step of comparing comprises comparing the result of the step of comparing to a threshold. In some embodiments, the threshold is a static (fixed) threshold, but in preferred embodiments, the threshold is a scale factor that is adjusted according to the expected size of the result of the step of comparing.

Preferably, the scale factor is adjusted based on a comparison of the result of the step of comparing and the result of the step of comparing for one or more previous measured positions of the device. Even more preferably, the scale factor is adjusted based on a comparison of the result of the step of comparing and an average or weighted average of the result of the step of comparing for a plurality of previous measured positions of the device.

The method can further comprise the step of discarding the measured position of the device from further analysis if it is determined that the measured position of the device is erroneous. In some embodiments, the further analysis can comprise determining the position of the device relative to a predefined geofence.

According to a second embodiment of the invention, there is provided a computer program product, comprising computer readable code embodied therein, the computer readable code being configured such that, on execution by a suitable computer or processor, the computer or processor is caused to perform any of the methods described above.

According to a third aspect of the invention, there is provided an apparatus, comprising a processor configured to determine the state of motion of a user of a device from a plurality of possible states; predict the position of the device using a plurality of models and the determined state of motion of the user, each model corresponding to a respective one of the plurality of possible states; obtain a measurement of the position of the device from position measurement means; compare the predicted position of the device to the measured position of the device; and determine whether the measured position of the device is erroneous based on the result of the comparison.

In some embodiments, the apparatus is configured as a device to be worn or carried by a user, with the device further comprising the position measurement means for obtaining measurements of the position of the device. In alternative embodiments, the apparatus is a separate device to the device that is worn or carried by a user.

Preferably, the plurality of possible states comprises two or more of the user sitting down, lying down, standing still, walking, running and traveling in a vehicle.

Preferably, the processor is configured to determine the state of motion of the user by analysing signals from one or more sensors and/or one or more earlier measured positions of the device. In these embodiments, the device additionally comprises one or more sensors. In some embodiments, the signals from one or more sensors comprise signals from one or more of an accelerometer, magnetometer and gyroscope.

In some embodiments, the processor is configured to determine the state of motion of the user by analysing the signals from the one or more sensors to identify signals indicative of footsteps by the user and/or the orientation of the user.

In some embodiments, the processor is configured to predict the position of the device using each of the plurality of models to estimate the next position of the device; weighting the estimate of the next position of the device obtained from each of the models according to the determined state of motion of the user; and combining the weighted estimates to determine the predicted position of the device.

In alternative embodiments, the processor is configured to predict the position of the device by selecting the one of the plurality of models corresponding to the determined state of motion of the user; and using the selected one of the plurality of models to determine the predicted position of the device.

In preferred embodiments, the plurality of models use dead-reckoning to estimate the position of the device. In further preferred embodiments, the plurality of models further use map data indicating roads and/or walkways to estimate the position of the device. This improves the accuracy of the predicted position of the device further by limiting the predicted position to positions that are consistent with the determined state of motion of the user (i.e. on the road if determined to be traveling in a vehicle and on a walkway if determined to be on foot—whether standing, walking or running).

Preferably, the processor comprises a Kalman filter, and the processor is configured to predict the position of the device using a plurality of models, the determined state of motion of the user and a current state of the Kalman filter.

Preferably, in a Kalman filter, the result of the comparison of the predicted position of the device to the measured position of the device is used to update the current state of the Kalman filter.

Preferably, the processor is configured to determine whether the measured position of the device is erroneous by comparing the result of the comparison to a threshold. In some embodiments, the threshold is a static (fixed) threshold, but in preferred embodiments, the threshold is a scale factor that is adjusted by the processor according to the expected size of the result of the comparison.

Preferably, the scale factor is adjusted by the processor by comparing the result of the comparison and the result of the comparison for one or more previous measured positions of the device. Even more preferably, the scale factor is adjusted by the processor by comparing the result of the comparison and an average or weighted average of the result of the comparison for a plurality of previous measured positions of the device.

The processor can be further configured to discard the measured position of the device from further analysis if it is determined that the measured position of the device is erroneous. In some embodiments, the further analysis by the processor can comprise determining the position of the device relative to a predefined geofence.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Although the invention will be described below with reference to position measurements obtained using a satellite positioning system (e.g. GPS), it will be appreciated that portable or mobile electronic devices can also or alternatively make position measurements using signals other than those received from a set of satellites, and it will be appreciated that the processing algorithm according to the invention is applicable to identifying outlier position measurements obtained using other types of positioning system, such as those that analyse received Wi-Fi network signals and/or analyse Cell IDs of cells in a mobile communication network near to the device.

Figure 1:
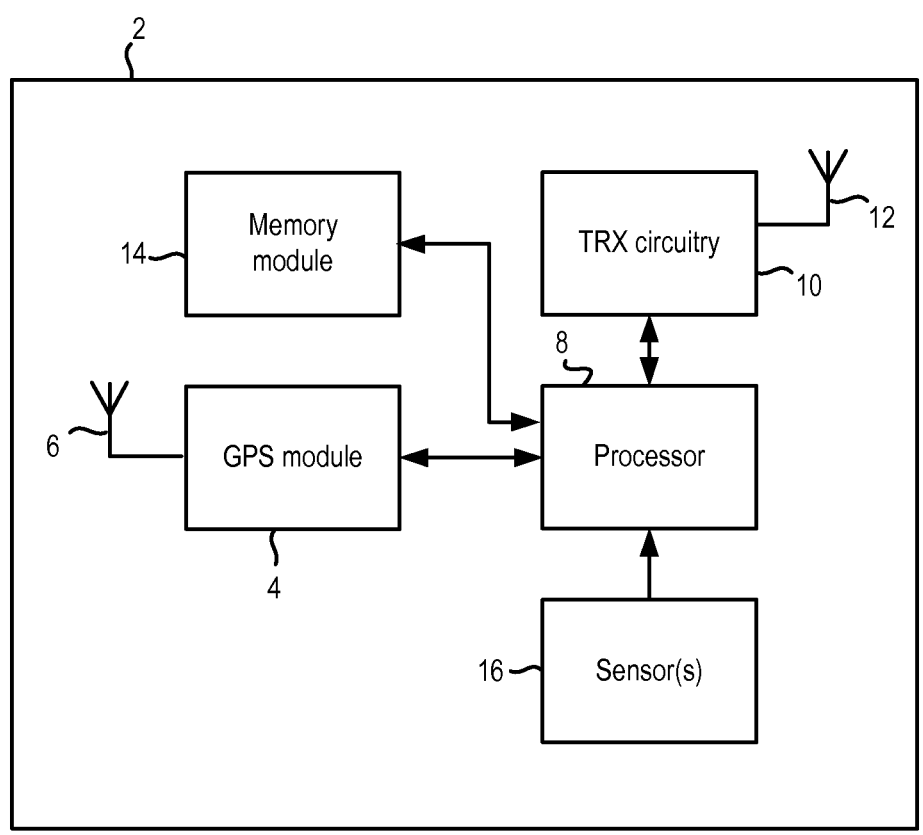
FIG. 1 is a block diagram of a device according to an embodiment of the invention.

An exemplary device according to an embodiment of the invention is shown in FIG. 1. In this embodiment, the device 2 is a mobile telephone or smartphone, although it will be appreciated that in other embodiments the device 2 can take a different form, such as a personal emergency response system (PERS) device, a mobile PERS device, a user-worn fall detector for monitoring whether a user has suffered a fall, or a satellite navigation system for use in a vehicle.

The device 2 comprises a satellite positioning system receiver 4, which in this embodiment is a GPS module 4 (although it will be appreciated that the device 2 can alternatively include receivers for other types of satellite positioning systems (such as Galileo or GLONASS) or receivers for receiving signals (such as Wi-Fi or cellular signals) from other sources that can be processed to determine the position of the device 2), coupled to an antenna 6 that receives the signals from the GPS satellites. The GPS module 4 is connected to a processor 8 that controls the general operation of the device 2.

As the device 2 in this embodiment is a mobile telephone or smartphone, the device 2 further comprises transceiver circuitry 10 and associated antenna 12 for communicating wirelessly with a mobile communication network.

The device 2 further comprises a memory module 14 that can store program code for execution by the processor 8 to cause the processor 8 to perform the processing required to control the device 2 according to the invention. The memory module 14 can also store one or more recent measurements of the position of the device 2 obtained by the GPS module 4.

In the illustrated embodiment, the device 2 further comprises one or more sensors 16 that can be used to determine the behaviour of the user of the device 2 (and in particular the state of motion of the user). Such behaviour can include the user standing still, sitting or lying down, walking, running or traveling in a vehicle. Suitable sensors 16 include an accelerometer, gyroscope and/or magnetometer. In embodiments where the sensor 16 is an accelerometer, the accelerometer 16 outputs a signal indicating the acceleration acting on the device 2 in one, two or three dimensions. In this case, the output of the accelerometer 16 at each sampling instant is provided in the form of a one, two or three dimensional vector, $(a_x, a_y, a_z)$. The accelerometer 16 can measure the acceleration with a sampling rate of 30 or 50 Hz, although it will be appreciated that other sampling rates can be used.

The current behaviour (state of motion) of the user of the device 2 can be estimated by analysing the signals from the one or more sensors 16, and/or by analysing previous measurements of the position of the device 2. For example, it is possible to identify steps by the user of the device 2 (e.g. in the form of the impact of the user's foot with the ground) from a signal from an accelerometer 16 and to determine from the magnitude and frequency of the steps whether the user is walking or running. The step detection can be combined with an analysis of previous position measurements to determine the speed that the user is moving. A signal from an accelerometer can also be used to identify when the user is traveling in a vehicle, since the signal will exhibit accelerations and decelerations that cannot be achieved by a user traveling on foot. As with the step detection, this analysis of the accelerometer signal can be combined with an analysis of previous position measurements to determine the speed that the user/device 2 is moving. A standing still, sitting or lying down state of the user can be determined from the lack of any significant non-gravitational acceleration in the signal from an accelerometer, along with a determination of the posture or orientation of the user using the accelerometer signal (and/or a signal from a gyroscope). Again, the analysis of the accelerometer and/or gyroscope signal can be combined with an analysis of previous position measurements to determine the speed of the user/device 2. In each case above, the state of motion detection can be made using just an analysis of previous position measurements (for example if the device 2 does not include the one or more sensors 16), since this will give an approximate speed of the user/device 2, and this speed can be correlated to an appropriate model. Those skilled in the art of GPS, accelerometer and gyroscope signal processing will be aware of ways in which the above processing can be implemented, for example from "Using Mobile Phones to Determine Transportation Modes" by Sasank Reddy et al, ACM Transactions on Sensor Networks, Vol. 6, No. 2, Article 13; "Classifying means of transportation using mobile sensor data" by T. Nick, Neural Networks (IJCNN), 18-23 Jul. 2010, pages 1-6; or "Detection of posture and motion by accelerometry: a validation study in ambulatory monitoring" by F. Foerster et al., Computers in Human Behaviour, Vol. 15, Issue 5, 1 Sep. 1999, pages 571-583.

Figure 2:
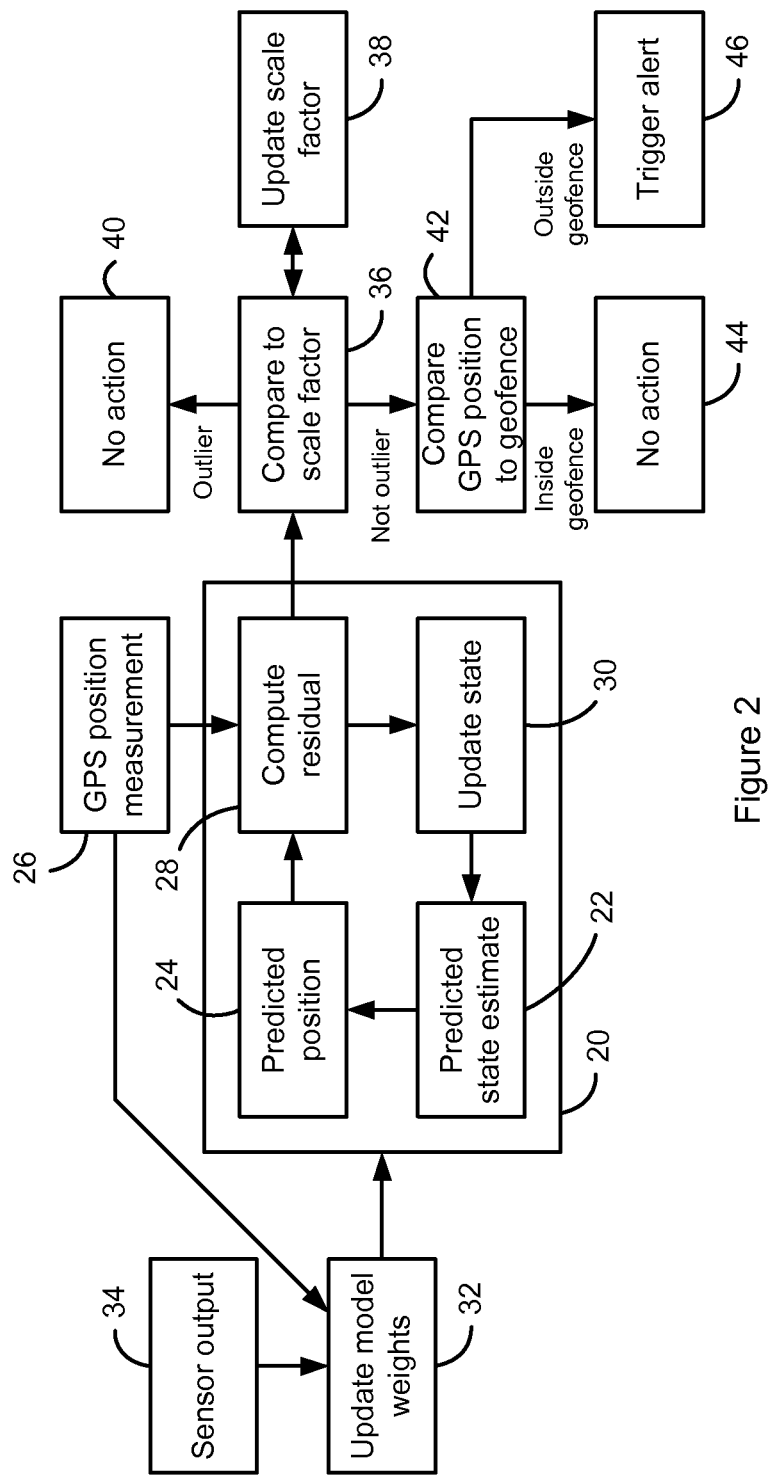
FIG. 2 is a block diagram illustrating the processing performed on position measurements according to an embodiment of the invention.

FIG. 2 is a block diagram illustrating the processing performed by the processor 8 according to an embodiment of the invention to identify outlier position measurements.

The processing performed by the processor 8 according to the invention is based around a Kalman filter 20. A Kalman filter 20 repeatedly goes through a number of steps: first, based on the current state of the Kalman filter 20, a prediction is made about the next state of the filter 20 (block 22). The state of the Kalman filter 20 represents a position and typically other variables too such as a heading, altitude, speed, etc), so the predicted state will be a new position, heading, altitude, speed, etc for the device 2 after some time interval. The prediction of the next state of the filter 20 is determined using a suitable model (for example a dead-reckoning model that takes the current state of the filter 20—including a position, heading and speed—and determines the new position by assuming that the user/device 2 will continue in a straight line in its current heading and speed). Those skilled in the art will appreciate that alternative types of model can be used.

Next, the predicted state is converted into a predicted position (block 24). Where the state predicted in block 22 comprises a position, heading, altitude, speed, etc, the conversion between blocks 22 and 24 can comprise extracting the position part of the state to provide the predicted position. Alternatively, block 24 can provide more than just the predicted position (which can be provided as a latitude and longitude measurement)—it can provide the heading, speed and/or the dilution of precision (DoP) from the GPS module 4.

The predicted position is then compared to an actual observation (i.e. the position 26 of the device 2 determined using the GPS module 4) and the residual is computed (block 28). The residual 28 is essentially the difference (e.g. distance) between the GPS position 26 and the predicted position 24. The residual 28 is used to determine a new state 30 of the filter 20. The filter process then repeats for a new GPS position measurement 26.

Updating the state of the filter 20 (block 30) results in the filter 20 having a state which typically corresponds to a state between the predicted position 24 and the observed GPS position 26. As known to those skilled in the art, the state of the filter 20 is updated using the Kalman gain.

GPS position measurements 26 that are erroneous or outliers (i.e. they are not representative of the actual position of the device 2) will likely result in a large residual at block 28, and this large residual feeds through to the new state 30 of the filter 20. Updating the state of the filter 20 in this way for a series of observed GPS positions 26 that are outliers causes the path to become smoothed out, reducing the impact of individual outlier measurements on the recorded path of the device 2.

Conventional usage of Kalman filters in GPS measurement processing can improve the accuracy of the predicted GPS position compared to non-Kalman filters. However, the positions predicted by conventional Kalman filters are still not always accurate enough to be used to identify outlier GPS measurements. In particular, poor prediction performance by the filter will result in high residuals at block 28, making it difficult to distinguish between valid GPS position measurements 26 and inaccurate (outlier) GPS measurements. Therefore, it is desirable for the accuracy of the predictions made by the filter 20 to be improved, thereby minimising the residual computed in block 28 and making outlier GPS position measurements easier to identify.

Therefore, in accordance with an aspect of the invention, to improve the positions predicted by the filter 20 at block 24, the filter 20 is adapted or selected based on the current behaviour (state of motion) of the user.

In particular embodiments, the filter 20 according to the invention can be an interacting multiple model Kalman filter (IMMKF). Whereas a typical Kalman filter has a single prediction function (used to calculate the new state 22 from the current state) and a single output function (to compute the observation (predicted position) 24), an IMMKF can comprise a plurality of models, each with separate prediction and output functions. The IMMKF can assign weights to the outputs of the multiple models to determine the influence of the multiple models on the final outcome (i.e. the residual 28 that is used to determine if the GPS position measurement 26 is an outlier) at a given time. The final outcome (i.e. the output of the IMMKF), is a weighted average of the outputs of the multiple models. The behaviour (state of motion) of the user estimated as described above is used to adapt or update the weights used in the IMMKF (block 32). The weights can be updated once a new predicted position is determined from the state estimate (i.e. after blocks 22 and 24 are completed). As described above, the behaviour estimation can be based on previous GPS position measurements 26 and/or outputs from one or more sensors 16 (with the outputs being represented by block 34 in FIG. 2). As an example, a likelihood can be determined for each possible state of motion of the user from the GPS measurements 26 and/or sensor outputs. This could be implemented using a hidden Markov model or a Bayesian belief network.

In alternative embodiments, multiple Kalman filters 20 can be provided, each having a prediction function and output function corresponding to a particular type of behaviour (state of motion) of the user. In these embodiments, the estimated behaviour of the user is used to select the most appropriate one of the filters 20 to use to determine if the measurement is an outlier. In this embodiment, it will be appreciated that multiple filters 20 will be provided, and the "update model weights" block 32 in FIG. 2 will be replaced by a 'model selection' or 'model enabling' block. The residual 28 of the selected filter 20 will be used in subsequent processing to determine if the GPS position measurement 26 is an outlier.

As described above, the behaviour of the user that can be determined and that can have a corresponding model in the IMMKF or in a respective Kalman filter includes the user standing still, sitting or lying down (in which case the model will typically predict the next state 22 to be similar to or the same as the current state), walking or running (in which case the model will typically limit the predicted state to positions that are reachable by a user moving on foot within the given timescale) or traveling in a vehicle (in which case the model can typically limit the predicted state to positions that are reachable by a user traveling in a vehicle). Those skilled in the art will be aware of suitable algorithms that can be used to determine the behaviour of the user. In each case, the models can be based on dead-reckoning, which means that the model predicts the next state of the filter 20 to be that obtained by the user moving in a straight line on the current heading and speed (in the case of the walking or running model, footsteps can be detected from accelerometer measurements and the detected footsteps used to estimate the speed and/or distance moved by the user).

As indicated above, a standing, sitting or lying down model can predict the next state 22 to be similar to or the same as the current state. As an alternative, as GPS usually suffers from measurement errors, another approach is to estimate the next state 22 from the most recent GPS positions with the assumption that these positions follow a normal distribution centred on the actual position (i.e. the mean of the distribution).

In conjunction with map data indicating roads and walkways, the walking, running and/or vehicle models can be further refined to limit the next predicted state/position to be a position that is on a walkway or road that the user is currently determined to be on (i.e. the user is predicted to continue on their current walkway or road by the distance derived from dead-reckoning).

Thus, as indicated above, adapting the weighting of an IMMKF or dynamically selecting an appropriate filter 20 from a plurality of filters 20 according to the current behaviour of the user improves the accuracy of the predicted position 24, and therefore reduces the residual computed in block 28.

To determine whether the current GPS position measurement 26 is an outlier, the residual 28 computed for that measurement is compared to a threshold (block 36).

In a simple embodiment, the threshold in block 36 is static (i.e. fixed). However, as the absolute error of the residual 28 scales with the distance traveled between GPS position measurements 26 being taken (i.e. absolute errors increase when the device 2 moves faster—assuming the sampling rate (i.e. the time between each GPS position measurement being obtained) does not change), it is desirable for the threshold in block 38 to be a scale factor that is adjusted according to the expected size of the residual 28.

Therefore, in a preferred embodiment, the threshold in block 36 is a scale factor that is updated (in block 38) based on a comparison of the current absolute error between the GPS position measurement 26 and the position predicted in block 24 (i.e. the residual 28) and the absolute error (i.e. residual 28) for one or more previous position measurements 26. In some embodiments, the current residual 28 is compared to the average (for example the mean or a weighted mean) of two or more of the residuals 28 for recent position measurements 26. A relatively high residual 28 compared to earlier residuals 28 leads to a higher scale factor 36 for assessing the next residual 28. The lower the residual (i.e. the better the model is at predicting the positions of the user), the lower the scale factor will be, meaning that an outlier measurement becomes easier to detect (since the scale factor/threshold is low). Conversely, when the model is less accurate in its predictions (perhaps because the user is traveling at high speed), the scale factor will increase to compensate.

If the residual 28 exceeds the static threshold or scale factor 36, the current GPS position measurement 26 is determined to be an outlier. In that case, although the residual calculated using the outlier GPS position measurement 26 is still used to update the state of the filter 20 (block 30), it is not used in any subsequent processing (as indicated by block 40). As indicated above, such processing can include determining whether the user/device 2 is inside or outside a permitted area (delineated by a geofence), reporting the position measurement to a remote location (for example if an alert has been triggered) and/or using the position measurement to illustrate the position or route that the user/device 2 is taking or has taken on a map.

If the residual 28 does not exceed the static threshold or scale factor 36, the current GPS position measurement 26 can be processed normally (i.e. it is not regarded as an outlier). In the illustrated embodiment, this processing comprises comparing the GPS position measurement 26 to a geofence (block 42) to determine whether the user/device 2 is inside or outside a permitted area. If the user is determined to be inside the permitted area, no action is taken (block 44). However, if the user is determined to be outside the permitted area, an alert can be triggered (block 46). This alert can comprise an audible and/or visible warning to the user of the device 2 that they are outside the permitted area, and/or it can comprise initiating a call or alert to a remote monitoring station (such as a call centre) using the transceiver circuitry 10 and associated antenna 12. As indicated above, the processing can also or alternatively include reporting the position measurement to a remote location (for example if an alert has been triggered) and/or using the position measurement to illustrate the position or route that the user/device 2 is taking or has taken on a map.

Although FIG. 2 illustrates that the processing according to the invention is performed by the processor 8 in the device 2, it will be appreciated that in alternative embodiments, the GPS module 4 can be configured to implement the processing according to the invention to identify outlier position measurements. In a further alternative embodiment, the processing according to the invention can be performed in a device that is remote from the device 2 that is carried or worn by the user, in which case the device 2 can be configured to transmit the position measurement data and any data collected using the one or more sensors 16 to the remote device.

There is therefore provided an improved technique for processing position measurements to identify measurements that are inaccurate or outliers.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of detecting erroneous measurements of a position of a device, the device comprising position measurement means, the method comprising:
    determining a state of motion of a user of the device from a plurality of possible states;
    predicting a predicted position of the device using a plurality of models, wherein each model has a separate prediction and output functions corresponding to a respective one of the plurality of possible states, and the determined state of motion of the user, wherein the predicting includes assigning weights to outputs of the plurality of models to determine an influence of each of the plurality of models on the predicted position;
    measuring a measured position of the device using the position measurement means;
    comparing the predicted position of the device to the measured position of the device; and
    determining whether the measured position of the device is erroneous based on a result of the step of comparing.

2. The method as claimed in claim 1, wherein the step of determining the state of motion of the user comprises analyzing signals from one or more sensors and/or one or more earlier measured positions of the device.

3. The method as claimed in claim 1, wherein the step of predicting the position of the device further comprises using a current state of a Kalman filter.

4. The method as claimed in claim 1, wherein the step of determining whether the measured position of the device is erroneous based on the result of the step of comparing comprises comparing the result of the step of comparing to a threshold.

5. The method as claimed in claim 4, wherein the threshold is a scale factor that is adjusted according to the expected size of the result of the step of comparing.

6. The method as claimed in claim 4, wherein the threshold is a scale factor that is adjusted based on a comparison of the result of the step of comparing and an average or weighted average of the result of the step of comparing for one or more previous measured positions of the device.

7. The method as claimed in claim 1, further comprising the step of discarding the measured position of the device from further analysis if it is determined that the measured position of the device is erroneous.

8. The method as claimed in claim 7, wherein the further analysis comprises determining the position of the device relative to a predefined geofence.

9. A non-transitory computer readable medium comprising computer readable code embodied therein, the computer readable code being configured such that, on execution by a suitable computer or processor, the computer or processor is caused to perform the method defined in claim 1.

10. The method as claimed in claim 1, further comprising:
generating updated weights based on the weights and the predicted position; and
predicting another predicted position based at least on the updated weights.

11. The method as claimed in claim 1, wherein the step of predicting the position of the device further comprises using an interacting multiple model Kalman filter.

12. The method as claimed in claim 1, wherein determining the state of motion comprises analyzing previously acquired global positioning system (GPS) position measurements.

13. The method as claimed in claim 12, wherein determining the state of motion comprises determining a probability for each possible state of motion from the GPS position measurements.

14. An apparatus, comprising:
a processor configured to:
determine the state of motion of a user of a device from a plurality of possible states;
predict a predicted position of the device using a plurality of models, wherein each model with a separate prediction and output functions corresponding to a respective one of the plurality of possible states, and the determined state of motion of the user, wherein the predicting includes assigning weights to outputs of the plurality of models to determine an influence of each of the plurality of models on the predicted position;
obtain a measurement of the position of the device from position measurement means;
compare the predicted position of the device to the measured position of the device; and
determine whether the measured position of the device is erroneous based on the result of the comparison.

15. The apparatus according to claim 14 wherein the device comprises the position measurement means for obtaining measurements of the position of the device.

16. The apparatus according to claim 14 further comprising one or more sensors of a group comprising an accelerometer, magnetometer and gyroscope.

17. The apparatus according to claim 14 wherein the processor is further configured to determine the measured position of the device relative to a predefined geofence.

18. The apparatus according to claim 17 wherein the apparatus further comprises transceiver circuitry and associated antenna for sending an alert to a remote monitoring station in dependence of the determined measured position of the device relative to the predefined geofence.

19. The apparatus according to claim 18 wherein the apparatus is further arranged to report the measured position to the remote monitoring station.

* * * * *